(12) United States Patent
Luther et al.

(10) Patent No.: US 6,585,704 B2
(45) Date of Patent: Jul. 1, 2003

(54) METHOD OF RETAINING A TIP PROTECTOR ON A NEEDLE WITH A CURVED TIP

(75) Inventors: Ronald B. Luther, Newport Beach, CA (US); Charles W. Dickerson, Tustin, CA (US)

(73) Assignee: B. Braun Medical, Inc., Bethlehem, PA (US)

(*) Notice: Subject to any disclaimer, the term of this patent is extended or adjusted under 35 U.S.C. 154(b) by 0 days.

(21) Appl. No.: 09/772,506

(22) Filed: Jan. 29, 2001

(65) Prior Publication Data
US 2002/0103463 A1 Aug. 1, 2002

(51) Int. Cl.[7] ............................................. A61M 5/00
(52) U.S. Cl. ................... 604/263; 604/198; 604/192; 604/272; 128/919
(58) Field of Search ............................. 604/187, 263, 604/272, 273, 274, 198, 110, 192, 240; 128/919

(56) References Cited

U.S. PATENT DOCUMENTS

| | | | |
|---|---|---|---|
| 3,612,050 A | 10/1971 | Sheridan | |
| 4,518,383 A | * 5/1985 | Evans | 604/51 |
| 4,610,671 A | 9/1986 | Luther | |
| 4,675,006 A | 6/1987 | Hrushesky | |
| 4,790,817 A | 12/1988 | Luther | |
| 4,846,811 A | 7/1989 | Vanderhoof | 604/263 |
| 4,874,373 A | 10/1989 | Luther et al. | |
| 4,915,696 A | 4/1990 | Feimer | |
| 4,929,241 A | 5/1990 | Kulli | 604/263 |
| 4,952,207 A | 8/1990 | Lemieux | 604/164 |
| 4,964,854 A | 10/1990 | Luther | 604/166 |
| 5,015,241 A | 5/1991 | Feimer | |
| 5,015,242 A | * 5/1991 | Heifetz | 604/198 |
| 5,026,356 A | 6/1991 | Smith | |
| 5,049,136 A | 9/1991 | Johnson | 604/198 |
| 5,053,017 A | 10/1991 | Chamuel | 604/192 |
| 5,120,321 A | 6/1992 | Oksman et al. | 604/198 |
| 5,135,504 A | 8/1992 | McLees | |
| 5,147,327 A | 9/1992 | Johnson | 604/198 |
| 5,215,528 A | 6/1993 | Purdy et al. | 604/164 |
| 5,215,534 A | 6/1993 | De Harde et al. | |
| RE34,416 E | 10/1993 | Lemieux | 604/164 |
| 5,322,517 A | 6/1994 | Sircom et al. | 604/198 |
| 5,334,158 A | * 8/1994 | McLees | 604/110 |
| 5,344,408 A | 9/1994 | Partika | 604/192 |
| 5,348,544 A | 9/1994 | Sweeney et al. | |
| 5,403,283 A | 4/1995 | Luther | 604/164 |
| 5,403,296 A | * 4/1995 | Mohring et al. | 604/274 |
| 5,411,492 A | 5/1995 | Sturman et al. | |
| 5,423,766 A | * 6/1995 | Di Cesare | 604/192 |
| 5,531,701 A | 7/1996 | Luther | |
| 5,549,570 A | * 8/1996 | Rogalsky | 604/198 |
| 5,558,651 A | 9/1996 | Crawford et al. | 604/263 |
| 5,562,636 A | * 10/1996 | Utterberg | 604/263 |
| 5,569,217 A | 10/1996 | Luther | 604/280 |
| 5,584,809 A | * 12/1996 | Gaba | 604/110 |
| 5,601,536 A | 2/1997 | Crawford et al. | 604/263 |
| 5,662,610 A | * 9/1997 | Sircom | 604/110 |
| 5,683,370 A | 11/1997 | Luther et al. | |
| 5,695,477 A | 12/1997 | Sfikas | 604/241 |

(List continued on next page.)

FOREIGN PATENT DOCUMENTS

WO    WO 99/08742    2/1999

Primary Examiner—Ehud Gartenberg
Assistant Examiner—Frederick C. Nicolas
(74) Attorney, Agent, or Firm—Christie, Parker & Hale, LLP

(57) ABSTRACT

A system for retaining a tip protector on a needle having a curved portion or bend adjacent the tip. A Braun clip tip protector is used in combination with a small sleeve which fits around the needle such that it is free to slide towards the needle tip until stopped by the bend. In that stopped position, the tip protector covers the tip but cannot slide off the end of the needle.

21 Claims, 4 Drawing Sheets

U.S. PATENT DOCUMENTS

| | | | | |
|---|---|---|---|---|
| 5,697,907 A | | 12/1997 | Gaba | 604/110 |
| 5,735,827 A | | 4/1998 | Adwers et al. | 604/263 |
| 5,738,660 A | | 4/1998 | Luther | 604/164 |
| 5,738,665 A | | 4/1998 | Caizza et al. | 604/263 |
| 5,772,638 A | * | 6/1998 | Utterberg et al. | 604/263 |
| 5,843,048 A | * | 12/1998 | Gross | 604/264 |
| 5,871,470 A | * | 2/1999 | McWha | 604/158 |
| 5,873,864 A | | 2/1999 | Luther et al. | 604/280 |
| 5,879,337 A | | 3/1999 | Kuracina et al. | 604/192 |
| 5,882,337 A | | 3/1999 | Bogert et al. | 604/110 |
| 5,910,130 A | * | 6/1999 | Caizza et al. | 604/110 |
| 5,910,133 A | * | 6/1999 | Gould | 604/164 |
| 5,913,848 A | | 6/1999 | Luther et al. | |
| 5,925,020 A | * | 7/1999 | Nestell | 604/198 |
| 5,925,032 A | * | 7/1999 | Clemens | 606/1 |
| 5,957,893 A | | 9/1999 | Luther et al. | |
| 5,993,409 A | * | 11/1999 | Maaskamp | 604/22 |
| 6,003,556 A | * | 12/1999 | Brugger et al. | 138/89 |
| 6,004,294 A | | 12/1999 | Brimhall et al. | 604/164 |
| 6,004,296 A | | 12/1999 | Jansen et al. | 604/198 |
| 6,012,213 A | | 1/2000 | Chang et al. | 29/447 |
| RE36,885 E | | 9/2000 | Blecher et al. | 604/198 |
| 6,117,108 A | | 9/2000 | Woehr et al. | 604/110 |
| 6,165,157 A | * | 12/2000 | Dillon et al. | 604/263 |
| 6,210,373 B1 | * | 4/2001 | Allmon | 604/192 |
| 6,224,569 B1 | | 5/2001 | Brimhall | 604/164 |
| 6,287,278 B1 | * | 9/2001 | Woehr et al. | 604/110 |

* cited by examiner

US 6,585,704 B2

METHOD OF RETAINING A TIP PROTECTOR ON A NEEDLE WITH A CURVED TIP

BACKGROUND OF THE INVENTION

1. Field of the Invention

The invention relates in general to needles with modified tips used for example in spinal injections, and specifically to a method of retaining a tip protector for such a needle.

2. Description of the Related Art

Historically in the medical field, needles have been necessary in many procedures. Unfortunately the danger of accidental injury by needles has increased due to the risk of transmission of various blood borne diseases such as AIDS and Hepatitis. In many procedures the use of needles has been reduced or eliminated, but there remain many situations in which the use of a needle is unavoidable. In these cases, it is desirable to limit the danger of accidental injury to people by the needle as much as possible.

One such situation in which use of a needle has not been eliminated is the insertion of catheters into a patient's vein. The catheter is inserted into a patient's vein by a health care worker by using a handheld placement device which includes a sharp-tipped needle. The needle is positioned in the interior hollow portion of the catheter with its tip extending slightly beyond the edge of the catheter. The opposite end of the needle is connected to a hub which is capable of being held by the health care worker.

Once the catheter has been inserted into the vein of the patient, the needle is withdrawn, leaving the catheter in the patient's vein. Once the needle has been removed from the catheter, however, the sharp tip of the needle is exposed, and poses a threat to anyone who handles it thereafter. With the needle tip exposed, the health care worker or anyone else who handles the needle is in danger of being accidentally pricked by the needle, and possibly infected with any blood-borne diseases the patient may have been carrying.

Bent needles such as Huber, Husted, and Touhy needles may be used with similar catheters in procedures such as the injection of spinal anesthetics where it is desirable to keep tissue from being cored and jammed in the hollow tip of the needle. These needles are often used in conjunction with stylets which are inserted into the needle and block the opening in order to further help keep tissue from jamming the needle. The stylet is a thin, flexible rod with a tip shaped such that it provides a flat surface at the opening of the needle. A hub at the end opposite the tip may be grasped and used to remove the stylet from the hollow interior of the Huber or other needle.

Many tip protectors have been developed for straight catheter needles. One in particular as described in patent publication WO 99/08742 (also U.S. application Ser. No. 08/097,170) to Wynkoop et al. describes a tip protector commercially referred to as the "Braun clip." The Braun clip was developed for use with over-the-needle intra-venous catheters as described above. This particular device is adapted to fit within the hub of the catheter such that when the needle is withdrawn from inside the catheter, the Braun clip slides toward the sharp tip until it reaches a retaining element which holds the clip from sliding completely off the tip. The retaining element is positioned to stop the clip such that its shielding portion covers the sharp tip of the needle.

When used with a typical I.V. catheter needle, the Braun clip is retained from sliding off the end of the needle by crimping the needle near the sharp tip. Unfortunately, needles such as the Huber which are often used in conjunction with stylets cannot be crimped due to the need for free movement of the stylet within the space inside the hollow needle. Thus, it is desirable to have a method of retaining a tip protector on a needle with a bent tip such as a Huber needle.

SUMMARY OF THE INVENTION

It is therefore an object of the present invention to provide a method of retaining a tip protector on a needle with a bent or otherwise modified tip which does not involve crimping or otherwise altering the profile of the needle.

The present invention employs a tip protector device having a protector portion and a portion that slides on the needle but cannot slide past the needle bend and stops the protector portion in the desired protective position. In the present invention a preferred form of the slide portion includes a sleeve with an internal diameter slightly larger than the needle's outer diameter. The sleeve slides freely over the majority of the needle shaft, but not around the needle bend and off the end of the tip. The protector portion can be of a known clip type such as the Braun clip.

The length of the sleeve is also an important dimension. It should be such that the Braun clip is allowed to operate properly without falling off the end of the tip. If the sleeve is too long, the clip will be restrained from closing over the needle tip. If the sleeve is too short, it may slide around the bend and off the tip. The details of these dimensions and relationships are expanded in the detailed description below.

One advantage of the use of a sleeve as described herein is its ease of assembly. Once the sleeve has been properly sized, it can be easily slid onto the shaft of the needle in operative relationship with the Braun clip before attaching the needle hub or before bending the tip. Another advantage is the low cost of the part. A sleeve providing features and advantages of the present invention can be produced very economically.

When used with an over-the-needle catheter, the tip protector and the sleeve can initially be conveniently housed in a rear hub on the catheter.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENT

Figure 1:
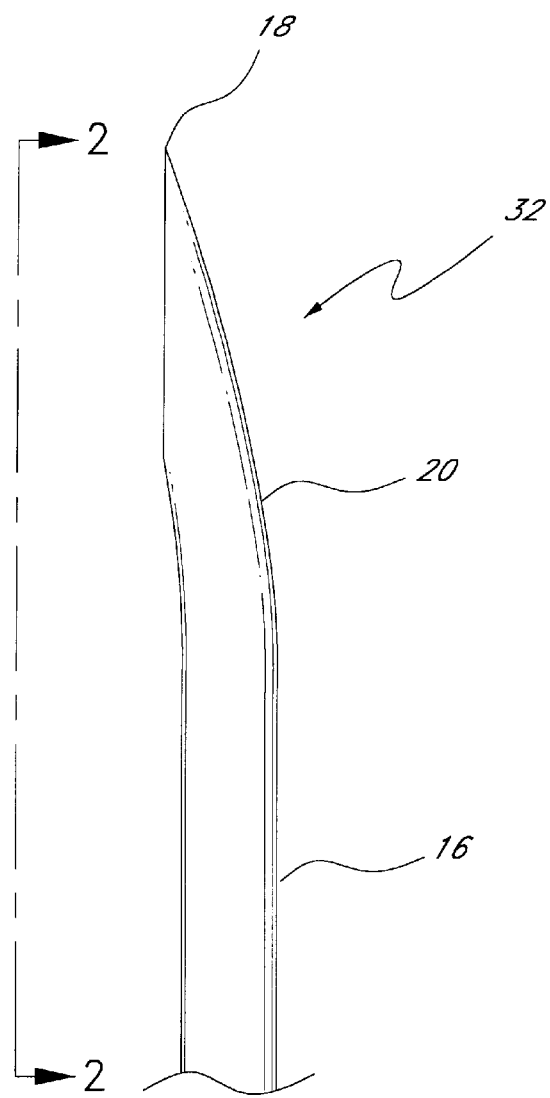
FIG. 1 is a side view of a Huber needle illustrating its curvature.
Figure 2:
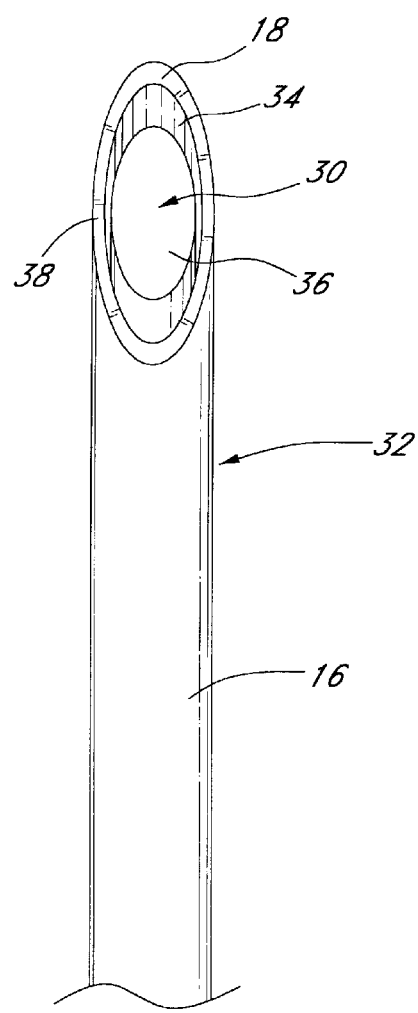
FIG. 2 is a front view of the Huber needle of FIG. 1 showing a stylet as it is typically positioned within the needle.

FIGS. 1 and 2 show a Huber needle 32 characterized by a curve or bend 20 in the tip. The bend allows the edge 38 of the opening 34 at the tip of the needle to be parallel to the axis of the needle 32. This helps to prevent tissue from being cored, and lodged in the hollow needle, and thereby clogging it. This type of needle is typically used in cases when a health care provider needs to inject fluids, sometimes including drugs, into areas protected by substantially hard tissues, such as the spine or the chest.

In order to additionally guard against tissue being cored by the needle, a Huber needle is typically used with a stylet 30 as shown in FIG. 2. The stylet 30 is typically a small, flexible rod which slides into the hollow interior of the needle 32. The tip of the stylet 30 is typically ground to a flat face 36 which is substantially co-planar with the edge 38 surrounding the opening 34 of the needle 32. The features and advantages of the present invention may also be realized in association with other types of needles with bent tips, such as Husted or Touhy needles. These are typically differentiated by the degree of their respective bends, and the present invention may be practiced with these other needles in the same manner as with the Huber needle.

Figure 7:
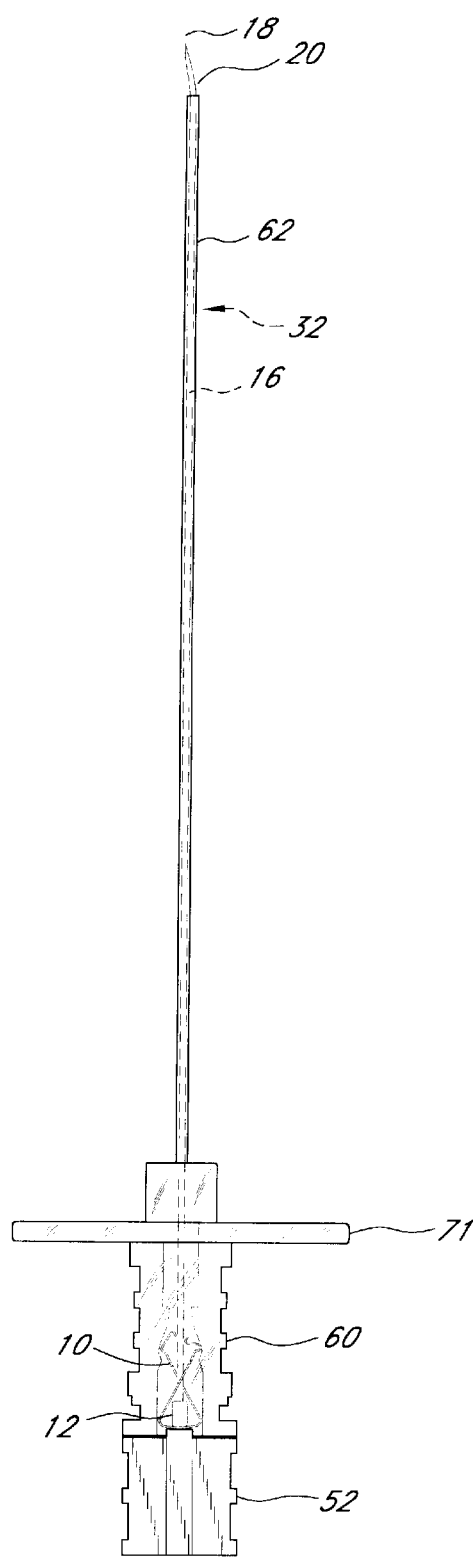
FIG. 7 is a side view of the device of FIGS. 4 and 5 in combination with an over-the-needle catheter.

An over-the-needle catheter 62 like the one shown in FIG. 7 is typically used to inject fluids, often containing medicines into the body of a patient. Over-the needle catheters are typically formed from relatively flexible plastics, and are typically disposed on a straight metal needle which is used to pierce the skin and any other tissue in order to locate the open end of the catheter in the particular part of the body to which the fluids are to be delivered. In typical use, a Huber needle 32 with an over-the-needle catheter 62 is grasped by the handle 71 and inserted for example, into the spine. Once the health care provider has determined that the tip 18 of the needle 32 and catheter 62 are in the correct location, the needle 32 is withdrawn from the patient (not shown), leaving the catheter 62 in the desired location. According to the present invention, when the needle 32 is withdrawn, a tip protector 10 and retaining slide or sleeve 12 preferably contained within the hub 60 of the catheter 62 will preferably be slid to the tip 18 of the needle 32 and stop, thereby covering the sharp tip 18 and protecting anyone handling the needle 32 from injury.

Figure 3:
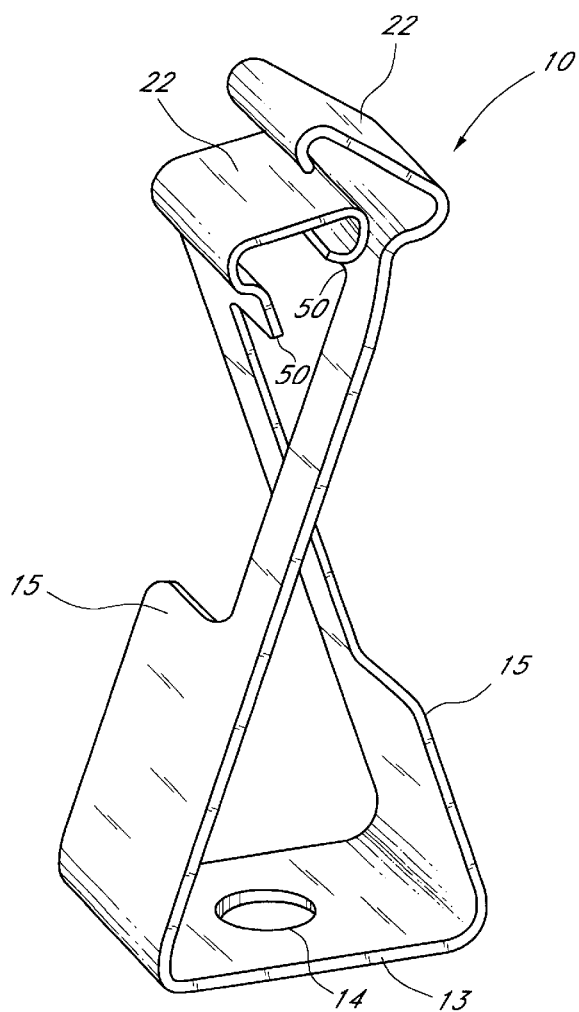
FIG. 3 is an orthogonal view of a Braun clip tip protector.

FIG. 3 shows a Braun clip 10 preferably punched from a substantially resilient material which will allow the clip to be substantially "springy" when used as described herein, and then bent into the shape shown. Alternatively, the clip 10 may be machined or cast, or made by any other process known to those skilled in the art. The hole 14 in the base 13 of the clip 10 is preferably sized such that it will fit over the needle 32 and allow the clip 10 to slide freely along the needle 32. The distance from the base 13 and the shielding portion 22 of the clip 10 can be considered the operative length of the clip 10. The Braun clip 10 is schematically shown and described herein, and reference can also be made to pending U.S. application Ser. No. 08/097,170 (also WO 99/08742) which is incorporated herein by reference.

Figure 4:
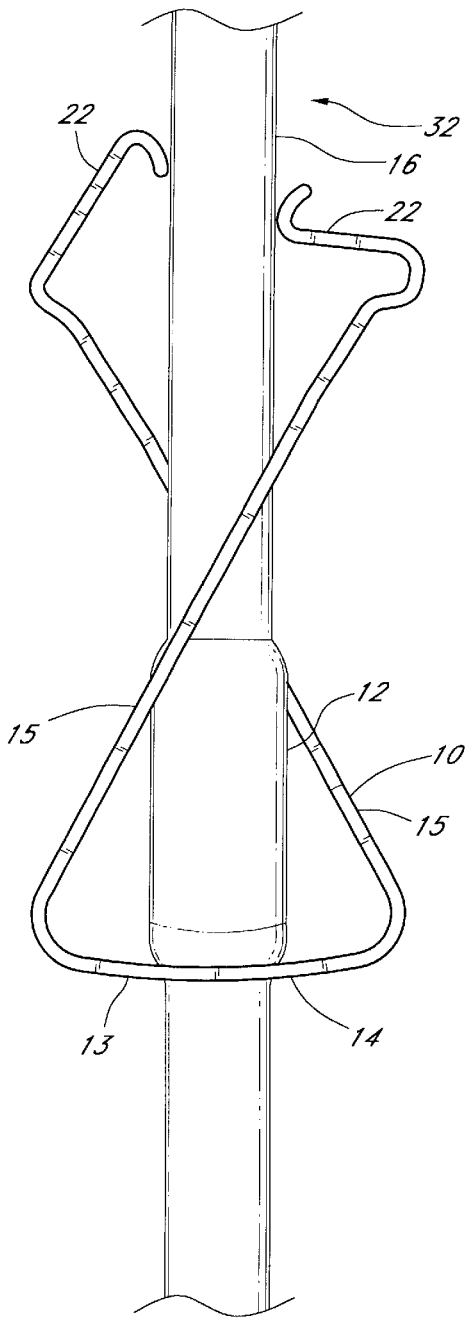
FIG. 4 is a side view of a tip protector and retaining sleeve positioned along the shaft of the needle, and having features and advantages of the present invention.
Figure 5:
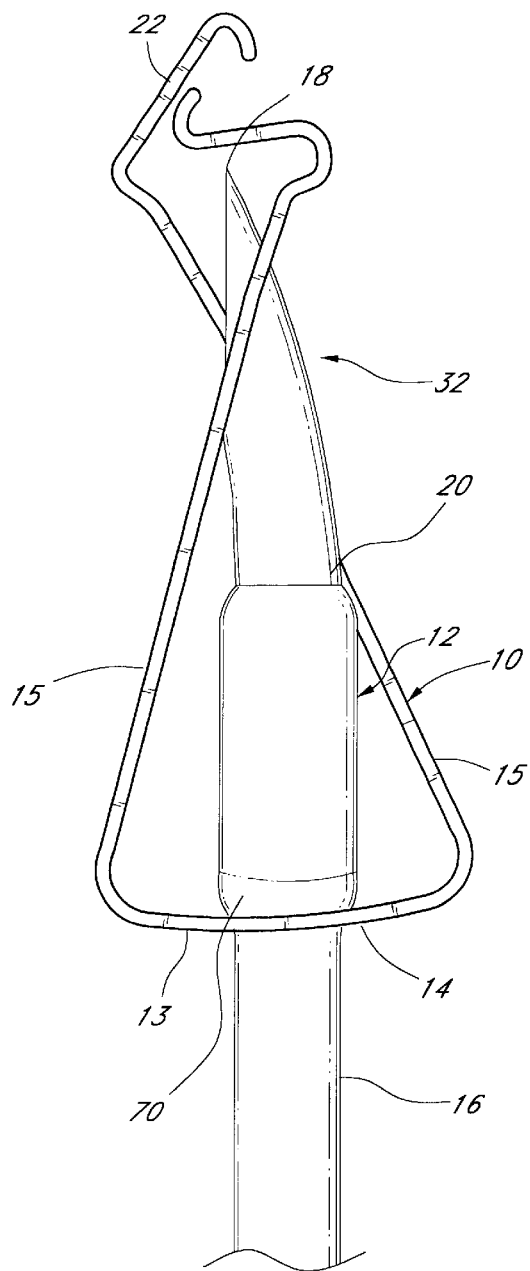
FIG. 5 is a side view of a tip protector and retaining sleeve positioned so as to cover the sharp needle tip, and having features and advantages of the present invention.

FIGS. 4 and 5 illustrate the Braun clip tip protector 10 and the retaining sleeve 12 as they are preferably disposed relative to one another and the needle 32 in accordance with the present invention. In FIG. 5 the shielding portion 22 of the clip 10 is covering the sharp tip 18 of the needle 32.

The retaining sleeve 12 preferably has a substantially circular cross section. Alternatively, the sleeve 12 may have any one of a variety of cross-sectional shapes such as elliptical, triangular, square, or any other polygonal shape providing that it functions as described herein. The retaining sleeve 12 may be made from a variety of substantially rigid materials, such as metal, glass, or substantially rigid polymers.

The size of the retaining sleeve 12 is preferably determined by the gauge of the needle 32, the size and angle of the bend 20, and the size of the clip 10 being used. The inner diameter of the retaining sleeve 12 is preferably 0.0001 to 0.003 inch larger than the outer diameter of the needle 32. If the inner diameter of the sleeve 12 is too small, the sleeve 12 of course will not slide properly. Conversely, if it is too large, the sleeve 12 will be allowed to slide past the bend 20 of the needle 32, thus allowing the clip 10 to fall off and thereby failing to protect a person from the sharp needle tip 18. The outer diameter of the sleeve 12 is preferably larger than the hole 14 in the base 13 of the clip 10 (shown in FIG. 3).

The sleeve 12 is preferably long enough that it is unable to slide around the bend 20 in the needle 32, but short enough that it allows the shielding portion 22 of the clip 10 to close over the sharp tip of the needle 32. The clip 10 is also preferably restrained from sliding far enough over the tip that the flanges 50 (shown in FIG. 3) pass the sharp tip 18 as this would allow the tip to be exposed.

Referring to FIG. 5, the relationship between the various dimensions of the clip 10 and the sleeve 12 are important to obtain the described result. Proper dimensions are preferably chosen based on the gauge of the needle 32 and the degree and length of the bend 20. The clip 10 and sleeve 12 are also preferably sized relative to one-another such that they will perform as described herein. For example, the distance between the sharp tip 18 of the needle 32 and the sleeve bottom end 70, when the sleeve 12 reaches the position at which it is stopped by the bend 20, should correspond with the operative length of the Braun clip 10 in such a way that the two lengths are substantially equal to one another (as shown in FIG. 5). The operative length of the clip 10 being defined as the distance between the clip base 13 and the shielding portion 22 of the clip 10.

The sleeve 12 is preferably held in operative relation to the clip 10 by the geometry of the clip 10 itself, and is preferably not physically attached thereto. If desired, however, the sleeve 12 may be glued, welded, or otherwise permanently bonded to the clip 10 in the operative relationship shown and described herein. Alternatively, the clip 10 and sleeve 12 may be formed integrally from the same piece of material by machining, casting, or any other method known to those skilled in the art.

Figure 6:
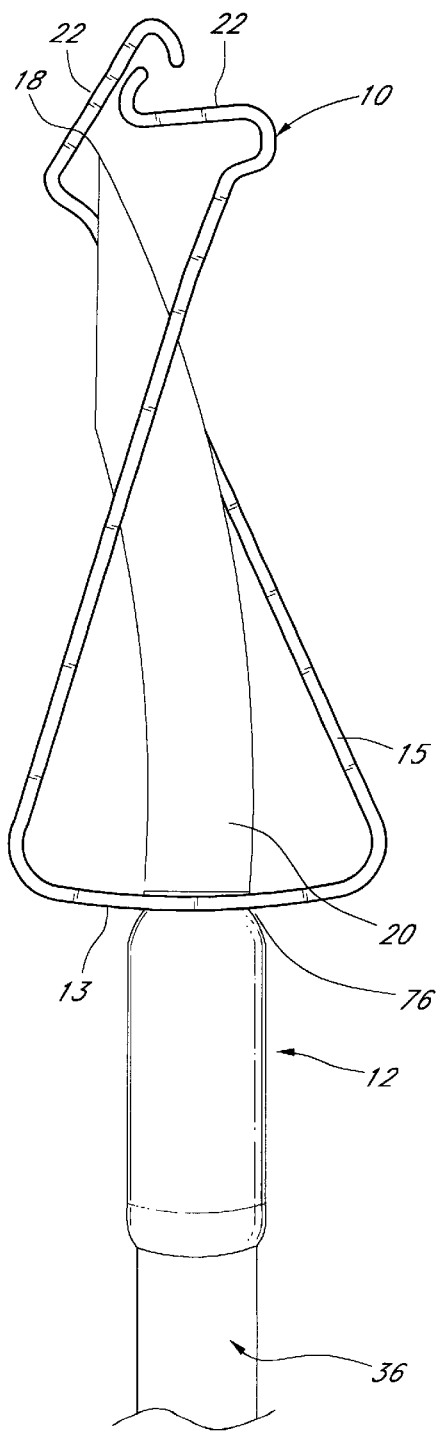
FIG. 6 illustrates an alternate relationship between the sleeve and a tip protector.

In an alternative embodiment as shown in FIG. 6, the sleeve 12 may be attached to the underside 76 of the base 13 of the clip 10. In this embodiment, the operative length of the clip 10 should be substantially equal to the distance between the end of the sleeve 12 attached to the clip underside 76 and the sharp tip 18 when the sleeve 12 is in its stopped position. Thus, with a sleeve and clip dimensioned like that of FIG. 5, the needle bend would have to be spaced further from the tip. Of course, clip and sleeve dimensions can be changed to fit a particular curved needle. The sleeve may be bonded with a weld, glue or other known method, and it is preferably made from a substantially rigid material such as plastic, metal, glass, etc. This embodiment is useful when the bent section of the needle is particularly long.

Thus, it may be seen that in either arrangement of FIGS. 5 or 6, the sleeve 12 and the clip 10 are configured to interengage in a manner that the sleeve stops movement of the clip in a position in which the clip shielding portion 22 properly covers the needle tip.

FIG. 7 illustrates a Braun clip-type protector 10 with a retaining sleeve 12 and an over-the-needle catheter 62 in typical use. The Braun clip 10 and the appropriately positioned retaining sleeve 12 are preferably contained within the hub 60 of the catheter 62 and positioned at the base 52 of the needle 32 while the needle 32 and catheter 62 are being inserted into the patient. When the needle 32 is withdrawn, the tip protector 10 and retaining sleeve 12 slide along the shaft 16 of the needle 32 toward the tip 18 of the needle 32. When the tip protector 10 and retaining sleeve 12 reach the position shown in FIG. 5, the retaining sleeve 12 is preferably stopped by the bend 20 in the needle 32. The stopped sleeve 12 in turn preferably stops the sliding of the clip 10 by contact between the two at the clip base 13. In this position (as shown in FIG. 5), the shielding portion 22 of the Braun clip 10 covers the sharp tip 18 of the needle 32 in order to guard a person from being accidentally injured.

If desired, the clip 10 can be disengaged, and both parts 10 and 12 may be slid back down to the base 38 of the needle 32, and a catheter 62 may be replaced. In order to move the clip 10 from the position shown in FIG. 5 to that shown in FIG. 4, the health care provider may pinch the sides 15 of the clip 10 until the two sides of the shielding portion 22 are sufficiently separated that they will allow the clip 10 to slide over the tip 18 and down the shaft 16 of the needle.

As will be recognized by those skilled in the art, the features and advantages of the present invention may be realized in association with any tip protector with which the invention is compatible, and are not limited to the Braun clip tip protector.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A device for protecting a sharp tip of a medical needle having a bend in its shaft, comprising:
    a needle tip protector including a protective portion configured to cover the needle tip to prevent a person from being stuck by the tip, and including a slide portion configured to slide along said shaft to a protective position in which the protective portion covers the needle tip and the slide portion is stopped by said bend to prevent the protective portion from moving beyond the protective position, and wherein the bend defines a first needle axis upstream of the bend and a second different needle axis downstream of the bend.

2. The device of claim 1 wherein the slide portion further includes a length that cooperates with an outer diameter of said shaft to prohibit said slide portion from sliding beyond said bend.

3. The device of claim 2 wherein said slide portion has an inner diameter which is between 0.0001 and 0.003 inch larger than the needle outer diameter.

4. The device of claim 2 wherein said slide portion includes a sleeve slidably mounted on said shaft.

5. The device of claim 4 wherein said sleeve and said tip protector are formed integrally from a single piece of material.

6. The device of claim 4 wherein said sleeve has a substantially elliptical cross section.

7. The device of claim 4 wherein said sleeve has a substantially polygonal cross section.

8. The method of claim 1 wherein said protective portion is part of a clip configured such that it could slide around the bend in the needle if it were not for said slide portion.

9. A device comprising:
    a needle having a shaft with a bend adjacent a sharp tip;
    a tip protector slidably mounted on said shaft;
    a sleeve comprising a length sized such that it may slide freely over said shaft, but may not slide around said bend, the length of said sleeve being selected to stop said sleeve at a location which prohibits said tip protector from sliding off said needle and which allows said tip protector to cover said sharp tip; and
    wherein the bend defines a first needle axis upstream of the bend and a second different needle axis downstream of the bend.

10. The device of claim 9 wherein said sleeve is positioned between a portion of said tip protector and said sharp tip.

11. The device of claim 10 wherein the inner diameter of said sleeve is 0.0001 to 0.003 inches larger than the outer diameter of said needle.

12. The device of claim 9 wherein said sleeve is substantially rigidly attached to said tip protector.

13. The device of claim 9 wherein said sleeve and said tip protector are formed integrally from a single piece of material.

14. The device of claim 9 wherein said sleeves is attached to a base of said tip protector on a side opposite said sharp tip.

15. A method of preventing needle stick for a needle having a bend in its shaft adjacent a sharp tip of the needle, comprising the steps of:
    positioning on the needle a tip protector having a protective portion configured to cover the tip and a slide portion configured to move on the needle towards the tip until it is stopped by the bend;
    interengaging the protective portion with the slide portion so that the protective portion covers the tip when the movement of the slide portion towards the tip is stopped by the bend; and
    wherein the bend defines a first needle axis upstream of the bend and a second different needle axis downstream of the bend.

16. The method of claim 15 including positioning the slide portion between a portion of the protector and the needle tip.

17. A needle tip protector device comprising a spring clip having an opening and a sleeve coaxially disposed over a needle having a shaft and a bend in the shaft, wherein the sleeve comprises a length and a cross-sectional dimension that are sized to be stopped by the bend, and wherein the bend defined two different needle axes.

18. The needle tip protector of claim 17, wherein the spring clip further comprises an end wall, a first side, a second side, and at least one arm extending in the direction of the second side of the end wall, and wherein the sleeve is positioned adjacent the second side of the end wall when coaxially disposed over the needle.

19. The needle tip protector of claim 17, wherein the spring clip further comprises an end wall, a first side, a second side, and at least one arm extending in the direction of the second side of the end wall, and wherein the sleeve is positioned adjacent the first side of the end wall when coaxially disposed over the needle.

20. The needle tip protector of claim 18, wherein the sleeve is attached to the second side of the end wall.

21. The needle tip protector of claim 19, wherein the sleeve is attached to the first side of the end wall.

\* \* \* \* \*